(12) United States Patent
Katz et al.

(10) Patent No.: US 11,452,485 B2
(45) Date of Patent: Sep. 27, 2022

(54) ELECTROANATOMICAL MAP RE-ANNOTATION

(71) Applicant: BIOSENSE WEBSTER (ISRAEL) LTD., Yokneam (IL)

(72) Inventors: Natan Sharon Katz, Kiryat Bialik (IL); Benjamin Cohen, Haifa (IL); Lior Zar, Poria Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 346 days.

(21) Appl. No.: 16/531,396

(22) Filed: Aug. 5, 2019

(65) Prior Publication Data

US 2021/0038171 A1 Feb. 11, 2021

(51) Int. Cl.
| | |
|---|---|
| *A61B 5/00* | (2006.01) |
| *A61B 5/349* | (2021.01) |
| *A61B 5/339* | (2021.01) |
| *A61B 5/287* | (2021.01) |

(52) U.S. Cl.
CPC ............ *A61B 5/7485* (2013.01); *A61B 5/287* (2021.01); *A61B 5/339* (2021.01); *A61B 5/349* (2021.01); *A61B 5/6859* (2013.01); *A61B 2562/0209* (2013.01)

(58) Field of Classification Search
None
See application file for complete search history.

(56) References Cited

U.S. PATENT DOCUMENTS

| | | |
|---|---|---|
| 6,301,496 B1 | 10/2001 | Reisfeld |
| 8,285,377 B2 | 10/2012 | Rosenberg |
| 8,346,372 B2 | 1/2013 | Yang |
| 8,527,049 B2 | 9/2013 | Koh |
| 9,125,585 B2 | 9/2015 | Rosenberg |
| 9,662,033 B2 * | 5/2017 | Severino ............... A61B 5/316 |

(Continued)

FOREIGN PATENT DOCUMENTS

| | | |
|---|---|---|
| EP | 3026639 A1 | 6/2016 |
| EP | 3453323 A1 | 3/2019 |

OTHER PUBLICATIONS

Search Report from corresponding European Patent Application No. 20189347.6 dated Dec. 17, 2020.

*Primary Examiner* — John R Downey
*Assistant Examiner* — Anant A Gupta
(74) *Attorney, Agent, or Firm* — Dergosits & Noah LLP; Todd A. Noah (57) ABSTRACT

A method, including receiving from mapping electrodes positioned at locations within a heart, signals indicating electrical activity in tissue contacting the electrodes, and processing the signals to identify, for each location, at least one corresponding LAT in a cycle of a heart. For each location, an earliest LAT in the cycle is identified, and an electroanatomical map including mapping points having respective locations and showing the earliest LAT at each location is generated and rendered. An input selecting a subset of the points is received, and a time range containing the earliest LAT of a majority of the points in the subset is identified. One or more outlying points in the subset are identified, and a second LAT, later than the earliest LAT in the cycle is found among the at least one identified LAT identified at the outlying points. The map is updated to display the found second LAT.

18 Claims, 5 Drawing Sheets

(56) References Cited

U.S. PATENT DOCUMENTS

| | | | |
|---|---|---|---|
| 2006/0276716 A1* | 12/2006 | Healey | A61B 5/361 |
| | | | 600/518 |
| 2016/0183877 A1* | 6/2016 | Williams | A61B 5/287 |
| | | | 606/41 |
| 2016/0324485 A1* | 11/2016 | Erdemir | A61B 5/6859 |
| 2017/0027524 A1 | 2/2017 | Du | |
| 2017/0251942 A1 | 9/2017 | Brodnick | |
| 2018/0042504 A1 | 2/2018 | Botzer | |
| 2018/0296108 A1 | 10/2018 | Stewart | |
| 2019/0035497 A1* | 1/2019 | Kolberg | A61B 5/00 |
| 2020/0085329 A1* | 3/2020 | Markovitz | A61B 5/287 |

* cited by examiner

ELECTROANATOMICAL MAP RE-ANNOTATION

FIELD OF THE INVENTION

The present invention relates generally to cardiac mapping, and specifically to re-annotating an area of an electroanatomical map.

BACKGROUND OF THE INVENTION

Cardiac arrhythmia, such as atrial fibrillation, is a heart rhythm that produces irregular heartbeats. Arrhythmias typically occur when regions of cardiac tissue abnormally conduct electric signals to adjacent tissue, thereby disrupting the normal cardiac cycle and causing asynchronous rhythm.

Mapping of electrical potentials in the heart is a commonly used tool for diagnosing and treating cardiac arrhythmias. Typically, time-varying electrical potentials in the endocardium are sensed and recorded as a function of position inside the heart, and then used to map a local electrogram or local activation time. The activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

U.S. Patent Application 2017/0251942 to Brodnick et al., describes a method for determining a local activation time (LAT) from at least three multi-channel cardiac electrogram signals including a mapping channel and a plurality of reference channels. The method includes collecting a mapping-channel signal and a first reference-channel signal to compute LAT values at a plurality of mapping-channel locations, monitoring the timing stability of the first reference-channel signal, and if the timing stability of the monitored signal falls below a stability standard, using the signal of a second reference channel to determine LAT values.

U.S. Patent Application 2018/0042504 to Botzer et al., describes a method for annotating a wavefront. The method includes receiving a bipolar signal from a pair of electrodes in proximity to a myocardium of a human subject, receiving a unipolar signal from a selected one of the pair of electrodes pre-processing electrode signals to remove of baseline wander, low pass filtering and any order of differentiation. The method also includes identifying candidate annotations in the signals, extracting features from the annotations, eliminating any candidate annotations meeting a criterion based on a feature threshold, eliminating any remaining candidate annotations that are insignificant relative to another very close activation, assigning a score to each remaining candidate annotation based on its feature values, and generating a map using the timing and features of any candidate annotations that surpass a score threshold.

U.S. Pat. No. 6,301,496 to Reisfeld describes a method for reconstructing a grid comprising multiple sampled points. The method includes applying stage of model distortion to the grid, in which the grid is roughly adjusted to the shape defined by the sampled points. The method also includes an iterative stage of flexible matching is carried out finely adjusting the grid points according to the coordinates of the sampled points. The method additionally includes applying one or more algorithms such as smoothing, an affine transformation and/or performing an exact matching stage which brings the grid to include substantially all the sampled points. Parameter values associated with the sampled points can be interpolated to all the grid points and the grid can be presented on a display.

U.S. Patent Application 2017/0027524 to Du et al., describes a method for detecting valid signals in a multi-channel mapping system that receives signals from multiple electrodes. The method includes acquiring a signal from a given electrode, calculating a first derivative of the signal, determining a minimum and maximum derivative from the first derivative, determining whether signs of the minimum and maximum derivative are different, and in response to determining whether the signs of the minimum and maximum derivative are different, displaying on a display apparatus whether the signal is valid.

The description above is presented as a general overview of related art in this field and should not be construed as an admission that any of the information it contains constitutes prior art against the present patent application.

Documents referenced in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention, a method including receiving in a computer, from an intracardiac catheter having a distal end including a plurality of electrodes positioned at respective locations within a heart of a subject, signals from the electrodes responsive to electrical activity in myocardial tissue with which the electrodes are in contact, processing the signals by the computer so as to identify, for each given location contacted by the electrodes, at least one corresponding local activation time (LAT) in a cycle of the heart, identifying by the computer, for each of the locations, an earliest LAT in the cycle, generating and rendering to a display an electroanatomical map including mapping points having respective locations and showing the earliest LAT at each location in the map, receiving in the computer an input selecting a subset of the mapping points, identifying, by the computer, a time range containing the earliest LAT of a majority of the mapping points in the subset, identifying, by the computer, one or more outlying mapping points in the subset for which the earliest LAT precedes the identified time range, finding, by the computer, among the at least one LAT identified at the outlying mapping points, a respective second LAT, later than the earliest LAT in the cycle of the heart, and updating and rendering the electroanatomical map to display the respective second LAT that was found at the one or more of the outlying mapping points.

In some embodiments, the intracardiac catheter includes a multi-spline catheter having at least one of the electrodes on each of the splines.

In additional embodiments, the signals include electrocardiogram signals.

In further embodiments, identifying the time range containing the earliest LAT of the majority of the mapping points in the subset includes applying a majority voting algorithm to the LATs in the subset.

In supplemental embodiments, the respective second LAT is within the identified time range.

In other embodiments, the step of updating and rendering the electroanatomical map is performed upon receiving an authorization signal.

There is also provided, in accordance with an embodiment of the present invention, an apparatus including a display, and a processor configured to receive, from an intracardiac catheter having a distal end including a plurality of electrodes positioned at respective locations within a heart of a subject, signals from the electrodes responsive to electrical activity in myocardial tissue with which the electrodes are in contact, to process the signals so as to identify, for each given location contacted by the electrodes, at least one corresponding local activation time (LAT) in a cycle of the heart, to identify, for each of the locations, an earliest LAT in the cycle, to generate and render to the display an electroanatomical map including mapping points having respective locations and showing the earliest LAT at each location in the map, to receive an input selecting a subset of the mapping points, to identify a time range containing the earliest LAT of a majority of the mapping points in the subset, to identify one or more outlying mapping points in the subset for which the earliest LAT precedes the identified time range, to find, among the at least one LAT identified at the outlying mapping points, a respective second LAT, later than the earliest LAT in the cycle of the heart, and to update and render the electroanatomical map to display the respective second LAT that was found at the one or more of the outlying mapping points.

There is further provided, in accordance with an embodiment of the present invention, a computer software product, operated in conjunction with an intracardiac catheter having a distal end including a plurality of electrodes for insertion into a heart of a subject, the product including a non-transitory computer-readable medium, in which program instructions are stored, which instructions, when read by a computer, cause the computer to receive, from the plurality of electrodes positioned at respective locations within the heart of the subject, signals from the electrodes responsive to electrical activity in myocardial tissue with which the electrodes are in contact, to process the signals so as to identify, for each given location contacted by the electrodes, at least one corresponding local activation time (LAT) in a cycle of the heart, to identify, for each of the locations, an earliest LAT in the cycle, to generate and render to the display an electroanatomical map including mapping points having respective locations and showing the earliest LAT at each location in the map, to receive an input selecting a subset of the mapping points, to identify a time range containing the earliest LAT of a majority of the mapping points in the subset, to identifying one or more outlying mapping points in the subset for which the earliest LAT precedes the identified time range, to find, among the at least one LAT identified at the outlying mapping points, a respective second LAT, later than the earliest LAT in the cycle of the heart, and to update and render the electroanatomical map to display the respective second LAT that was found at the one or more of the outlying mapping points.

BRIEF DESCRIPTION OF THE DRAWINGS

The disclosure is herein described, by way of example only, with reference to the accompanying drawings, wherein.

DETAILED DESCRIPTION OF EMBODIMENTS

When performing a medical procedure to produce an electroanatomical map of a heart chamber, a distal end of a mapping catheter is moved along myocardial tissue within the chamber, and signals from different measured positions are acquired. The signals are automatically analyzed to find their respective local activation times (LATs), and the electroanatomical map is generated and rendered so that the LATs are presented as different colors (i.e., for the different times) on a three-dimensional (3D) map of the chamber.

There may be instances where the automatic signal analysis generates some incorrect LAT values in the map. Embodiments of the invention provide methods and systems for correcting any incorrect LAT values that were generated by the automatic analysis. As described hereinbelow, upon receiving, from an intracardiac catheter having a distal end comprising a plurality of electrodes positioned at respective locations within a heart of a subject, signals from the electrodes responsive to electrical activity in myocardial tissue with which the electrodes are in contact, the signals are processed so as to identify, for each given location contacted by the electrodes, at least one corresponding LAT in a cycle of the heart. For each of the locations, an earliest LAT in the cycle is identified, and an electroanatomical map comprising mapping points having respective locations and showing the earliest LAT at each location in the map is generated and rendered to a display.

Subsequent to rendering the map, an input is received indicating a selected subset of the mapping points, and a time range is identified that contains the earliest LAT of a majority of the mapping points in the subset. One or more outlying mapping points in the subset for which the earliest LAT precedes the identified time range are identified, and among the at least one LAT identified at the outlying mapping points, a respective second LAT, later than the earliest LAT in the cycle of the heart, at one or more of the outlying mapping points is found. Finally the electroanatomical map is updated and rendered in order to display the respective second LAT that was found at the one or more of the outlying mapping points.

Electroanatomical maps may comprise mapping points based on a large number (possibly ~5,000) of signals. By automatically correcting any mapping points in selected regions, systems implementing embodiments of the present invention enable a medical professional to rapidly correct a subset (possibly ~100) of the mapping points that correspond to incorrect LAT values.

System Description

Figure 1A:
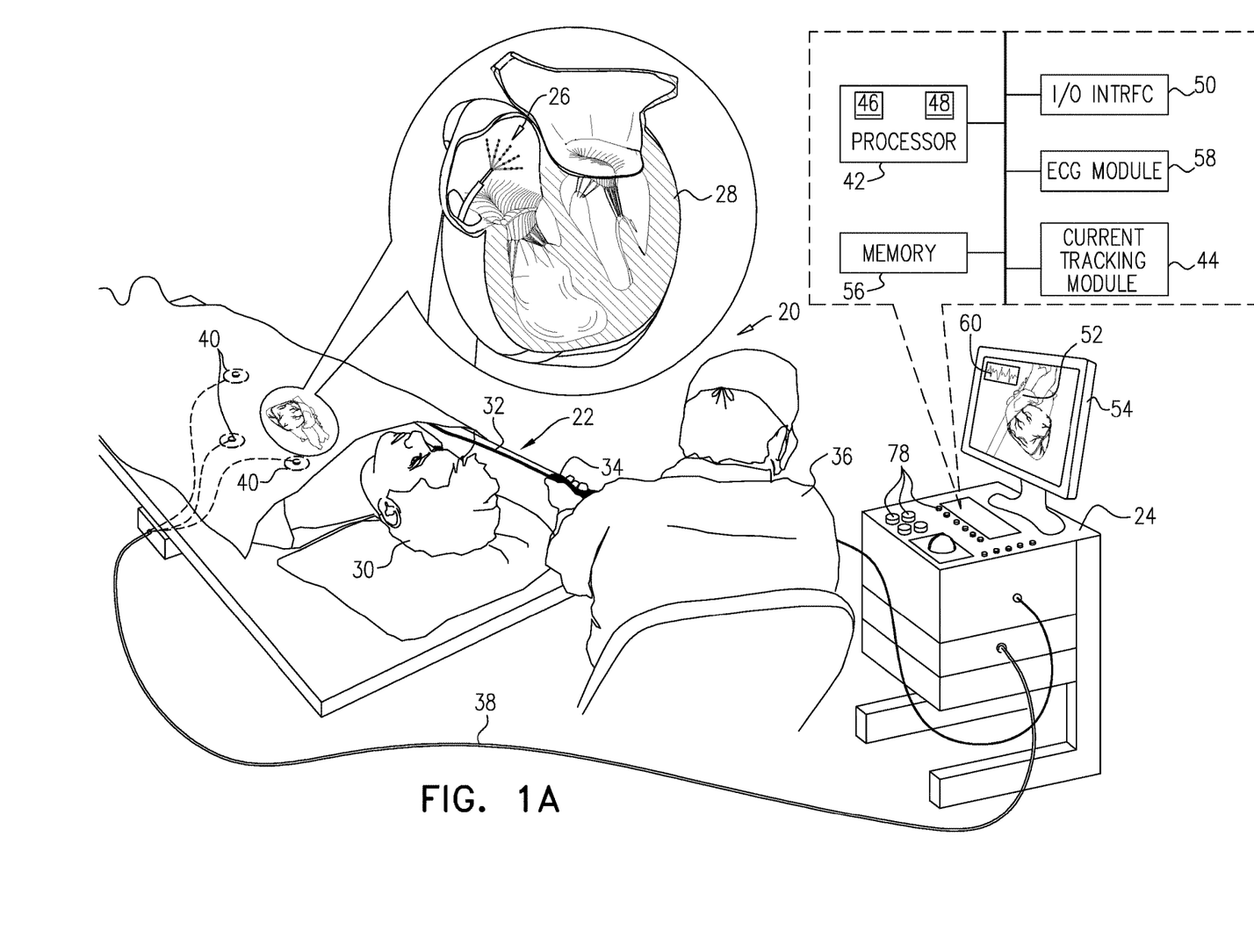
FIGS. 1A and 1B, are schematic, pictorial illustrations of a medical system comprising a mapping catheter, in accordance with an embodiment of the present invention.
Figure 1B:
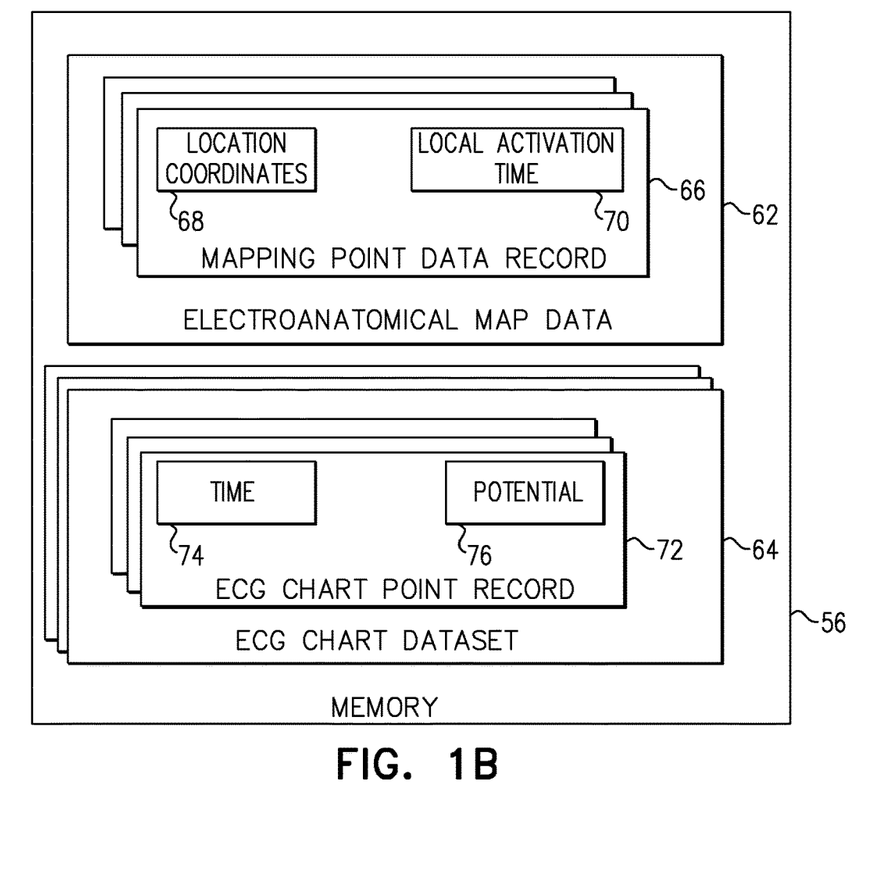
Figure 2:
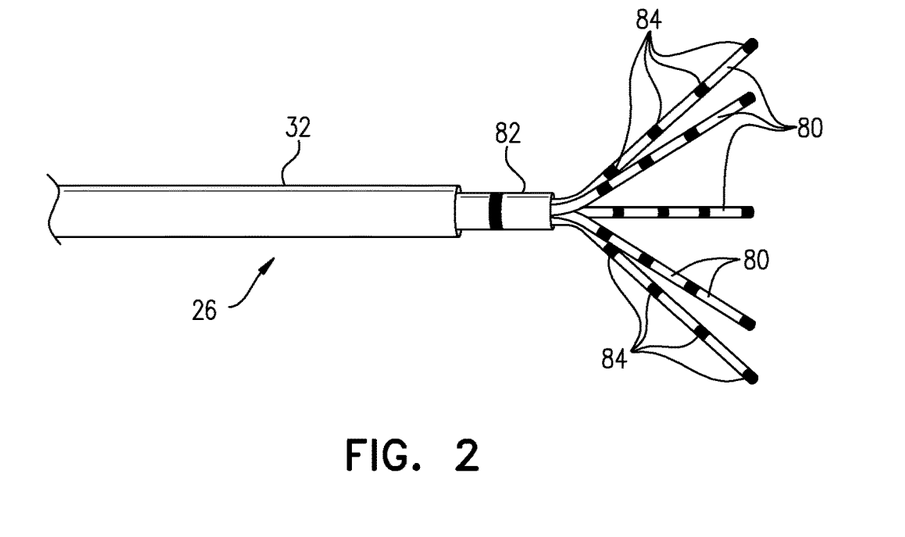
FIG. 2 is a schematic pictorial illustration of a distal end of the mapping catheter, in accordance with an embodiment of the present invention.

FIGS. 1A and 1B are schematic, pictorial illustrations of a medical system 20 comprising a medical probe 22 and a control console 24, and FIG. 2 is a schematic pictorial illustration of a distal end 26 of the medical probe, in accordance with an embodiment of the present invention. Medical system 20 may be based, for example, on the CARTO® system, produced by Biosense Webster Inc. (Diamond Bar, Calif., U.S.A.). In embodiments described hereinbelow, medical probe 22 can be used for diagnostic or therapeutic treatment, such as for such as mapping electrical potentials of a heart 28 of a patient 30. In embodiments described herein, medical probe 22 may also be referred to as a mapping catheter. Alternatively, medical probe 22 may be used, mutatis mutandis, for other therapeutic and/or diagnostic purposes in the heart or in other body organs.

Medical probe 22 comprises an insertion tube 32 and a handle coupled to a proximal end of the insertion tube. By manipulating handle 34, a medical professional 36 can insert probe 22 into a body cavity in patient 30. For example, medical professional 36 can insert probe 22 through the vascular system of patient 30 so that distal end 26 of probe 22 enters a chamber of heart 28 and engages myocardial tissue at a desired location or locations. By way of example, as shown in FIG. 2, distal end 26 of probe 22 comprises flexible splines 80 that are formed at the end of a tubular shaft 82. During a medical procedure, medical professional 36 can deploy splines 80 by extending tubular shaft from insertion tube 32.

Control console 24 is connected, by a cable 38, to body surface electrodes, which typically comprise adhesive skin patches 40 that are affixed to patient 30. Control console 24 comprises a processor 42 that, in conjunction with a current tracking module 44, determines position coordinates of distal end 26 inside heart 28 based on impedances measured between adhesive skin patches 40 and mapping electrodes 84 that are affixed to splines 80 as shown in FIG. 2. In embodiments described herein, electrodes 84 can also be configured to apply a signal to tissue in heart 28, and/or to measure a certain physiological property (e.g., the local surface electrical potential) at a location in the heart. Electrodes 84 are connected to control console 24 by wires (not shown) running through medical probe 22.

While embodiments herein show probe 22 comprising a multi-spline intracardiac catheter such as the Pentaray® NAV catheter, using other multi-electrode intracardiac catheters such as the Navistar® Thermocool® catheters are considered to be within the spirit and scope of the present invention. The Pentaray® NAV and Navistar® Thermocool® catheters are both produced by Biosense Webster Inc.

Processor 42 may comprise real-time noise reduction circuitry 46 typically configured as a field programmable gate array (FPGA), followed by an analog-to-digital (A/D) ECG (electrocardiograph) signal conversion integrated circuit 48. The processor can pass the signal from A/D ECG circuit 48 to another processor and/or can be programmed to perform one or more algorithms disclosed herein, each of the one or more algorithms comprising steps described hereinbelow. The processor uses circuitry 46 and circuit 48, as well as features of modules which are described in more detail below, in order to perform the one or more algorithms.

The medical system shown in FIGS. 1 and 2 uses impedance-based sensing to measure a location of distal end 26, other position tracking techniques may be used (e.g., techniques using magnetic-based sensors). Impedance-based position tracking techniques are described, for example, in U.S. Pat. Nos. 5,983,126, 6,456,864 and 5,944,022. The methods of position sensing described hereinabove are implemented in the above-mentioned CARTO® system and are described in detail in the patents cited above.

Control console 24 also comprises an input/output (I/O) communications interface 50 that enables the control console to transfer signals from, and/or transfer signals to electrodes 84 and adhesive skin patches 40. Based on signals received from electrodes 84 and/or adhesive skin patches 40, processor 42 can generate an electroanatomical local activation time (LAT) map 52 (FIG. 1A) that presents measurements of cardiac conduction velocity, as described in the description referencing FIG. 5 hereinbelow.

During a procedure, processor 42 can present electroanatomical LAT map 52 to medical professional 36 on a display 54, and store data representing the electroanatomical LAT map in a memory 56, as described in the description referencing FIG. 1A hereinbelow. Memory 56 may comprise any suitable volatile and/or non-volatile memory, such as random access memory or a hard disk drive. In some embodiments, medical professional 36 can manipulate map 52 using one or more input devices 78. In alternative embodiments, display 54 may comprise a touchscreen that can be configured to accept inputs from medical professional 36, in addition to presenting map 52.

Control console 24 may also comprise an electrocardiogram (ECG) module 58 that can be configured to generate an ECG chart from the signals received from electrodes 84. In some embodiments, processor 42 presents one or more ECG charts 60 on display 54 (i.e., along with LAT map 52), and store data representing the ECG chart map in memory 56.

As shown in FIG. 1A, memory 56 stores electroanatomical map data 62 that processor 42 can use to generate and render electroanatomical map 52, and stores ECG chart datasets 64 that the processor can use to generate and render ECG charts 60. Electroanatomical map data comprises a plurality of mapping point records 66, each of the mapping point records comprising a set of location coordinates 68 (i.e., in patient 30) and a local activation time (LAT) 70. In embodiments herein location coordinates 68 may also be referred to as locations 68.

Each ECG signal dataset 64 comprises multiple ECG chart point records 72, each of the ECG signal point records comprising a measurement time 74 and an electrical potential measurement 76. In embodiments herein, each given electrode 84 has a corresponding one-to-one correspondence with a given ECG chart dataset 64. In other words, each given ECG chart dataset 64 stores multiple ECG chart point records that stores electrical potential measurements 76 and measurement times 74 that processor 42 receives from its corresponding electrode 84.

Electroanatomical Map Generation and Re-Annotation

Figure 3:
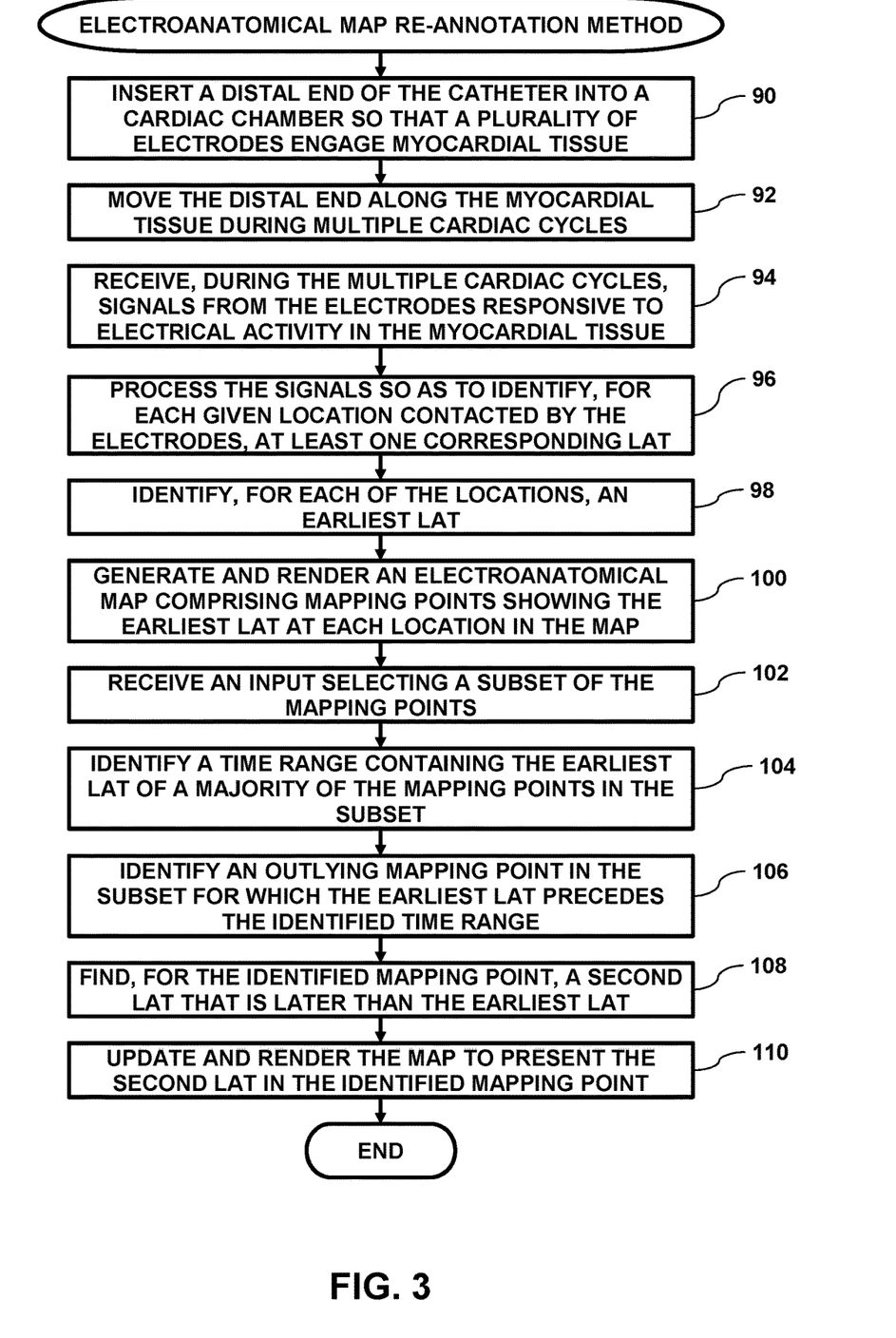
FIG. 3 is a flow diagram that schematically illustrates a method of generating and re-annotating an electroanatomical map based on signals received from the mapping catheter, in accordance with an embodiment of the present invention.
Figure 4:
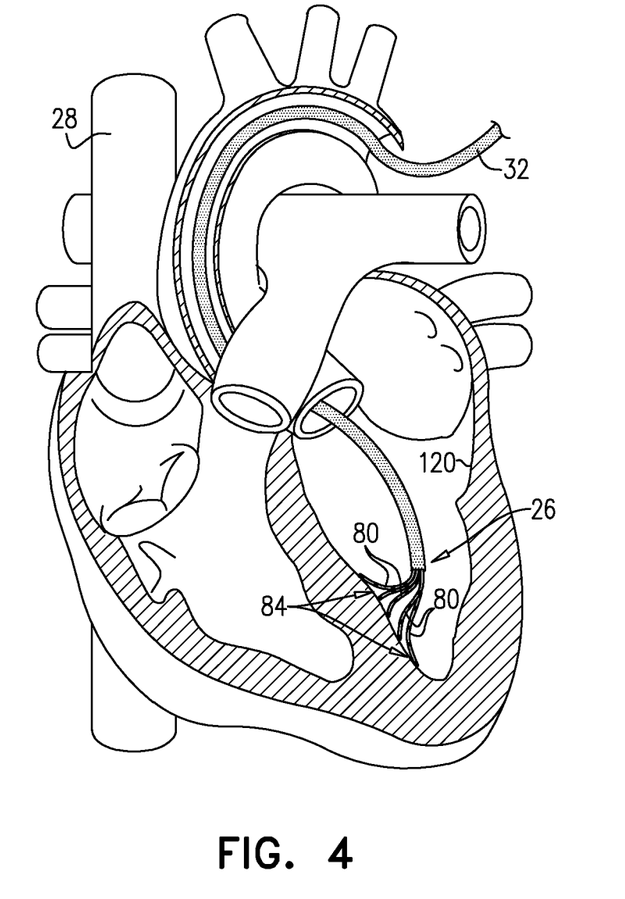
FIG. 4 is a schematic detail view of the distal end of the mapping catheter in the cardiac chamber during the mapping procedure, in accordance with an embodiment of the present invention.

FIG. 3 is a flow diagram that schematically illustrates a method for generating and re-annotating electroanatomical map 52 for a chamber of heart 28, and FIG. 4 is a schematic detail view of splines 80 engaging myocardial tissue 120 in the chamber, in accordance with an embodiment of the present invention.

In an insertion step 90, medical professional 36 inserts distal end 26 into the chamber so that splines 80 engage myocardial tissue 120, and in a maneuvering step 92, medical professional 36 moves the splines at the distal end along the myocardial tissue during multiple cardiac cycles. As medical professional 36 moves the splines along myocardial tissue 120 during the multiple cardiac cycles, processor 42 receives location signals that indicate impedances measured between adhesive skin patches 40 and electrodes 84.

In some embodiments, processor 42 can determine a given location of a given electrode 84 by conveying, to current tracking module 44, the location signals received from adhesive skin patches 40, and the current tracking module can compute the given location using embodiments described supra. Upon receiving the location signals from each given electrode 84, processor 42 can process the location signals to determine respective sets of location coordinates for the electrodes.

In a first receive step 94, processor 42 also receives (i.e., in addition to receiving the location signals), from electrodes 84 at respective sampling times, measurement signals responsive to electrical activity in myocardial tissue 120 with which the electrodes are in contact. In a processing step 96, processor 42 processes the measurement signals so as to identify, for each given set of location coordinates contacted by the electrodes, electrical potential values indicated by the measurement signals, and to identify at least one corresponding local activation time (LAT) in a cycle of heart 28.

Upon receiving and processing the mapping and location signals for a given electrode 84, processor 42 adds, to the corresponding ECG chart dataset, respective records 72 for each of the sampling times, and populates, for each added ECG chart point record 72, measurement time 74 with the respective sampling time, and potential measurement 76 with the respective electrical potential value. Upon storing and populating ECG chart datasets 64, processor 42 adds a new record 66 for each of the identified LATs, and populates, for each added mapping point data record 66 (i.e., corresponding to a given LAT), location 68 with the location coordinates of the corresponding LAT and LAT 70 with the sampling time of the corresponding LAT.

In a first identification step 98, processor 42 identifies, for each given set of location coordinates 68, an earliest of the LATs in the cycle. Typically, processor 42 identifies a single LAT 70 for each given set of location coordinates 68. However, there may be instances when processor 42 identifies more than one LAT 70 for each given set of location coordinates 68. ECG charts 60 showing single and multiple LATs are described in the description referencing FIG. 5 hereinbelow.

In a map generation step 100, processor 42 generates and renders to display 54 electroanatomical map 52 comprising mapping points having respective locations 68 and showing the earliest LAT 70 at each of the locations in the map.

Figure 5:
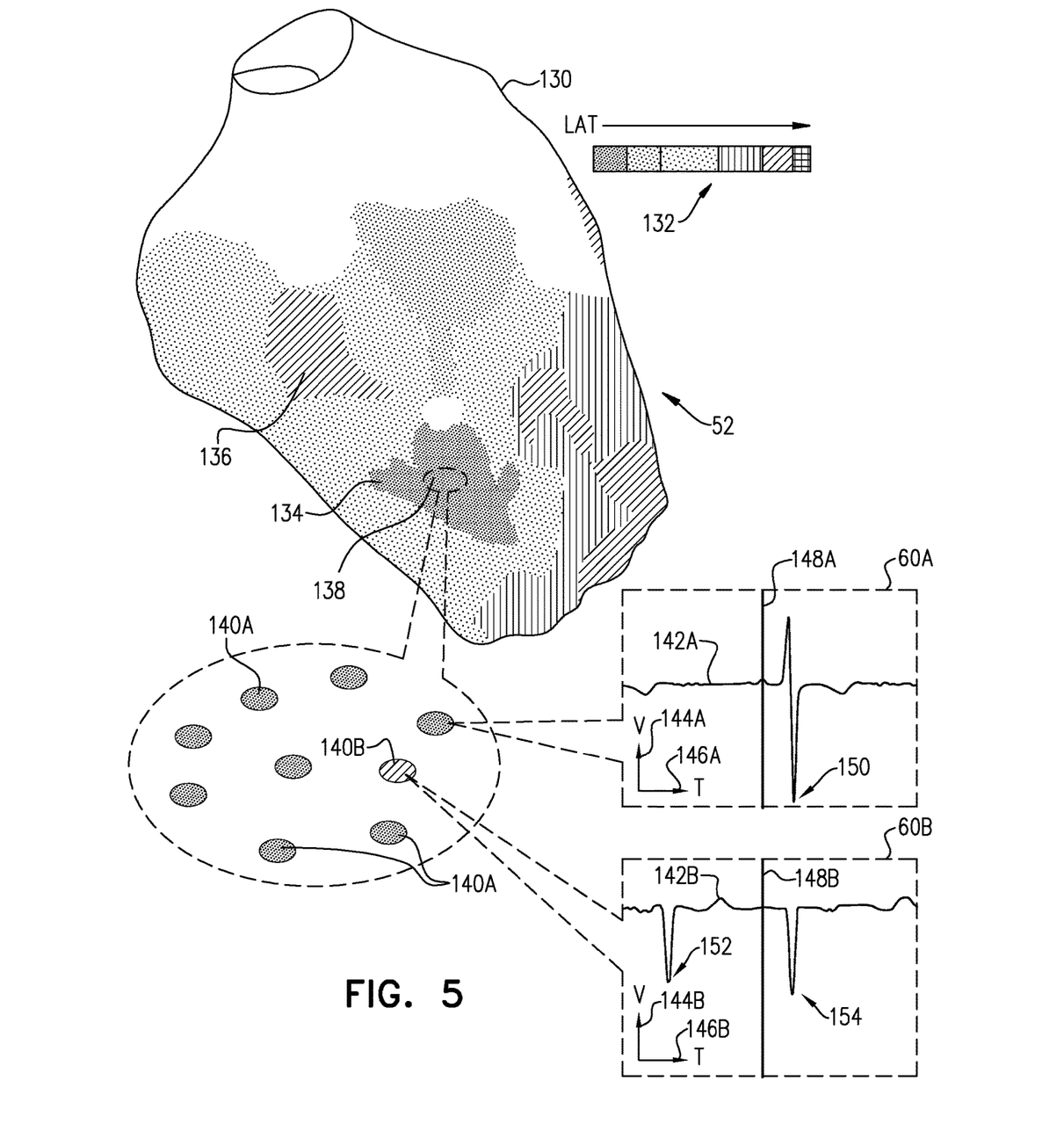
FIG. 5 is a schematic view of an electroanatomical map comprising a mapping point having an outlying local activation time, in accordance with an embodiment of the present invention.

FIG. 5 is a schematic pictorial illustration showing a section of LAT map 52 that comprises a physical map 130 of a chamber of heart 28, in accordance with an embodiment of the present invention. In FIG. 5, local activation time information for map 52 is incorporated into physical map 130 and coded using patterns in accordance with a key 132. These patterns simulate the pseudo-colors of an actual functional map. In this example map 52 comprises a first region 134 has a relatively short LAT, and a second region 136 that has a relatively longer local activation time.

LAT map 52 comprises multiple mapping points 140, each of the mapping points corresponding to a given set of location coordinates 68 and a given local activation time 70. In a selection step 102, processor receives an input (e.g., from input devices 78) selecting an area in the map comprising a subset 138 of the mapping points. In certain user interfaces, this input may comprise a "brush tool".

In a second identification step 104, processor 42 identifies a time range containing the earliest LAT of a majority of the mapping points in the subset. For example, processor 42 can use the Boyer-Moore majority voting algorithm to identify the time range. In FIG. 5, mapping points 140 correspond to respective ECG charts 60, and the mapping points, the ECG charts and respective elements of the ECG charts can be differentiated by appending a letter to the identifying numeral, so that mapping points 140A corresponds to ECG chart 60A and mapping point 140B corresponds to ECG chart 60B.

Each ECG chart 60 comprises a trace comprising a line 142 that plots potential measurements 76 along a vertical axis 144 against time along a horizontal axis 146, wherein the potentials are measured as voltages V and the time is measured in seconds S. In ECG charts 60, lines 142 show potential measurements 76 measured during a single cardiac cycle.

The ECG charts shown in FIG. 5 present local activation time in relation to a reference annotation 148. For example, mapping points 140A may correspond to ECG 60A that comprises an LAT point 150 that corresponds to a local activation time 70 that is (for purposes of this example) 10 ms after a time indicated by reference annotation 148A. In some embodiments, mapping points 140A may correspond to a first given LAT 70 with a tolerance of 10 ms+/−5 ms. In other words, processor 42 can present mapping points 140A for locations 68 whose local activation times 70 are within a time range of 5-15 ms subsequent to the time indicated by reference annotation 148A. In this case, in step 104, processor 42 identifies the time range as being 5-15 ms subsequent to the time indicated by reference annotation 148A. In some embodiments, the time range can be specified by medical professional 36.

In the example presented in FIG. 5, mapping point 140B may correspond to ECG 60B that comprises an LAT point 152 corresponding to a second given local activation time 70 that is (for purposes of this example) 50 ms prior to a time indicated by reference annotation 148B, and a LAT point 154 that corresponds to a second given local activation time 70 that is (for example) 11 ms subsequent to the time indicated by reference annotation 148B. As described supra, processor 42 uses the earliest LAT 70 for each set of location coordinates 68 to generate map 52. Therefore, mapping point 140A in map 52 corresponds to the LAT indicated by LAT point 152.

Returning to the flow diagram, in a third identification step 106, processor 42 identifies one or more outlying mapping points 60 in subset 138 for which the earliest corresponding LAT 70 precedes the identified time range. In the example shown in FIG. 5, processor 42 identifies mapping point 140B as the outlying mapping point. In this example, the location coordinates for mapping point 140B are within region 134, and the LAT for mapping point 140B (i.e., according to legend 132) is similar to the mapping points in region 136.

In a find step 108, processor 42 finds among the at least one LAT identified at the outlying mapping points, a respective second LAT, later than the earliest LAT in the cycle of the heart, at one or more of the outlying mapping points. In the example shown in FIG. 5, processor 42 identifies the LAT corresponding to LAT point 154 as the later LAT for the location corresponding to mapping point 140B. In some embodiments, the identified later LAT is within the time range identified in step 104.

Finally, in an update step 110, processor 42 updates and renders electroanatomical map 52 on display 54 to present the respective second LAT that was found at the one or more of the outlying mapping points, and the method ends. To update and render electroanatomical map 52, processor 42 can replace, on display 54, the pseudo-color for mapping point 140B with the same pseudo-color used for mapping points 140A.

In some embodiments, processor 42 can perform update step 110 upon receiving an authorization from medical professional 36. For example, upon identifying the second LAT in step 108, processor 42 can present the second LAT on display 54, and present a message on the display requesting authorization to update the map. Upon receiving an authorization message (e.g., from a given input device 78), processor 42 can update and render electroanatomical map 52 on display 54.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for electroanatomical map re-annotation, the method comprising:
receiving in a computer, from an intracardiac catheter having a distal end comprising a plurality of electrodes positioned at respective locations within a heart of a subject, signals from the electrodes responsive to electrical activity in myocardial tissue with which the electrodes are in contact;
processing the signals by the computer so as to identify, for each given location contacted by the electrodes, at least one corresponding local activation time (LAT) in a cycle of the heart;
identifying by the computer, for each of the locations, an earliest LAT in the cycle;
generating and rendering to a display an electroanatomical map comprising mapping points having respective locations and showing the earliest LAT at each location in the map, wherein the electroanatomical map comprises a physical map of a chamber of the heart and the LAT values are incorporated into the physical map;
receiving in the computer an input selecting a subset of the mapping points;
identifying, by the computer, a time range for the subset based upon the received input selection, the time range containing the earliest LAT of a majority of the mapping points in the selected subset;
identifying, by the computer, one or more outlying mapping points in the selected subset for which the earliest LAT precedes the identified time range;
finding, by the computer, among the at least one LAT identified at the outlying mapping points in the selected subset, a respective second LAT, later than the earliest LAT in the cycle of the heart; and
updating and rendering the electroanatomical map to display the respective second LAT that was found at the one or more of the outlying mapping points in the selected subset thereby automatically correcting any mapping points in selected subset, wherein the updated electroanatomical map, presented on the display, enables user correction of mapping points.

2. The method according to claim 1, wherein the intracardiac catheter comprises a multi-spline catheter having at least one of the electrodes on each of the splines.

3. The method according to claim 1, wherein the signals comprise electrocardiogram signals.

4. The method according to claim 1, wherein identifying the time range for the subset based upon the received input selection containing the earliest LAT of the majority of the mapping points in the subset comprises applying a majority voting algorithm to the LATs in the subset.

5. The method according to claim 1, wherein the respective second LAT is within the identified time range.

6. The method according to claim 1, wherein the step of updating and rendering the electroanatomical map is performed upon receiving an authorization signal.

7. An apparatus for electroanatomical map re-annotation, the apparatus comprising:
a display; and
a processor configured:
to receive, from an intracardiac catheter having a distal end comprising a plurality of electrodes positioned at respective locations within a heart of a subject, signals from the electrodes responsive to electrical activity in myocardial tissue with which the electrodes are in contact,
to process the signals so as to identify, for each given location contacted by the electrodes, at least one corresponding local activation time (LAT) in a cycle of the heart,
to identify, for each of the locations, an earliest LAT in the cycle,
to generate and render to the display an electroanatomical map comprising mapping points having respective locations and showing the earliest LAT at each location in the map, wherein the electroanatomical map comprises a physical map of a chamber of the heart and the LAT values are incorporated into the physical map,
to receive an input selecting a subset of the mapping points,
to identify a time range for the subset based upon the received input selection, the time range containing the earliest LAT of a majority of the mapping points in the selected subset,
to identify one or more outlying mapping points in the selected subset for which the earliest LAT precedes the identified time range,
to find, among the at least one LAT identified at the outlying mapping points in the selected subset, a respective second LAT, later than the earliest LAT in the cycle of the heart, and
to update and render the electroanatomical map to display the respective second LAT that was found at the one or more of the outlying mapping points in the selected subset thereby automatically correcting any mapping points in selected subset, wherein the updated electroanatomical map, presented on the display, enables user correction of mapping points.

8. The apparatus according to claim 7, wherein the intracardiac catheter comprises a multi-spline catheter having at least one of the electrodes on each of the splines.

9. The apparatus according to claim 7, wherein the signals comprise electrocardiogram signals.

10. The apparatus according to claim 7, wherein the processor is configured to identify the time range for the subset based upon the received input selection containing the earliest LAT of the majority of the mapping points in the subset by applying a majority voting algorithm to the LATs in the subset.

11. The apparatus according to claim 7, wherein the respective second LAT is within the identified time range.

12. The apparatus according to claim 7, wherein the processor is configured to perform step of updating and rendering the electroanatomical map upon receiving an authorization signal.

13. A computer software product, operated in conjunction with an intracardiac catheter having a distal end comprising a plurality of electrodes for insertion into a heart of a subject, the product comprising a non-transitory computer-readable medium, in which program instructions are stored, which instructions, when read by a computer, cause the computer:

to receive, from the plurality of electrodes positioned at respective locations within the heart of the subject, signals from the electrodes responsive to electrical activity in myocardial tissue with which the electrodes are in contact;

to process the signals so as to identify, for each given location contacted by the electrodes, at least one corresponding local activation time (LAT) in a cycle of the heart;

to identify, for each of the locations, an earliest LAT in the cycle;

to generate and render to the display an electroanatomical map comprising mapping points having respective locations and showing the earliest LAT at each location in the map, wherein the electroanatomical map comprises a physical map of a chamber of the heart and the LAT values are incorporated into the physical map;

to receive an input selecting a subset of the mapping points;

to identify a time range for the subset based upon the received input selection, the time range containing the earliest LAT of a majority of the mapping points in the selected subset;

to identifying one or more outlying mapping points in the selected subset for which the earliest LAT precedes the identified time range;

to find, among the at least one LAT identified at the outlying mapping points in the selected subset, a respective second LAT, later than the earliest LAT in the cycle of the heart; and to update and render the electroanatomical map to display the respective second LAT that was found at the one or more of the outlying mapping points in the selected subset thereby automatically correcting any mapping points in selected subset, wherein the updated electroanatomical map, presented on the display, enables user correction of mapping points.

14. The computer software product according to claim 13, wherein the intracardiac catheter comprises a multi-spline catheter having at least one of the electrodes on each of the splines.

15. The computer software product according to claim 13, wherein the signals comprise electrocardiogram signals.

16. The computer software product according to claim 13, wherein identifying the time range for the subset based upon the received input selection containing the earliest LAT of the majority of the mapping points in the selected subset comprises applying a majority voting algorithm to the LATs in the subset.

17. The computer software product according to claim 13, wherein the respective second LAT is within the identified time range.

18. The computer software product according to claim 13, wherein the step of updating and rendering the electroanatomical map is performed upon receiving an authorization signal.

* * * * *